United States Patent
Lee et al.

(10) Patent No.: US 9,963,684 B2
(45) Date of Patent: May 8, 2018

(54) FORMALDEHYDE DEHYDROGENASE AND METHOD FOR PREPARING FORMALDEHYDE USING SAME

(71) Applicants: KONKUK UNIVERSITY INDUSTRIAL COOPERATION CORP., Seoul (KR); Intelligent Synthetic Biology Center, Yuseong-gu, Daejeon (KR)

(72) Inventors: Jung-Kul Lee, Seoul (KR); Ranjitha Ramakrishnan, Seoul (KR); Ji-Hyun Park, Seoul (KR); Tae-Su Kim, Seoul (KR); Sun-Chang Kim, Daejeon (KR)

(73) Assignees: Konkuk University Industrial Cooperation Corp., Seoul (KR); Intelligent Synthetic Biology Center, Yuseong-gu, Daejeon (KR)

( * ) Notice: Subject to any disclaimer, the term of this patent is extended or adjusted under 35 U.S.C. 154(b) by 0 days. days.

(21) Appl. No.: 15/125,785

(22) PCT Filed: May 29, 2014

(86) PCT No.: PCT/KR2014/004812
§ 371 (c)(1),
(2) Date: Nov. 16, 2016

(87) PCT Pub. No.: WO2015/137565
PCT Pub. Date: Sep. 17, 2015

(65) Prior Publication Data
US 2017/0145389 A1 May 25, 2017

(30) Foreign Application Priority Data
Mar. 13, 2014 (KR) .......... 10-2014-0029848

(51) Int. Cl.
*C12P 7/04* (2006.01)
*C12N 9/02* (2006.01)
*C12N 15/52* (2006.01)
*C12P 7/24* (2006.01)

(52) U.S. Cl.
CPC ........... *C12N 9/0008* (2013.01); *C12N 15/52* (2013.01); *C12P 7/24* (2013.01); *C12Y 102/01046* (2013.01)

(58) Field of Classification Search
CPC ................................ C12N 9/0008; C12P 7/04
See application file for complete search history.

(56) References Cited

U.S. PATENT DOCUMENTS 6,440,711 B1 8/2002 Dave
2007/0042479 A1 2/2007 Dave et al.

FOREIGN PATENT DOCUMENTS

JP 06303981 A 11/1994
JP 2005185138 A 7/2005

OTHER PUBLICATIONS

Varga et al., UNiProt database, Accession No. J4QK49, Oct. 2012.*
"Aldehyde dismutase [Burkholderia multivorans]", NCBI, GenBank Accession No. WP_006396349.1, (2013), 1 pg.
"Formaldehyde dehydrogenase [Burkholderia multivorans ATCC 17616]", NCBI, GenBank Accession No. YP_001583515.1, (2013), 1 pg.
"International Application No. PCT/KR2014/004812, International Search Report dated Dec. 18, 2014", w/ English Translation, (Dec. 18, 2014), 8 pgs.
"International Application No. PCT/KR2014/004812, Written Opinion dated Dec. 18, 2014", (Dec. 18, 2014), 5 pgs.
Ma, KE, et al., "Enzyme Mediated Increase in Methanol Production from Photoelectrochemical Cells and CO2", ACS Catalysis 6.10, (2016), 6982-6986.

* cited by examiner

*Primary Examiner* — Maryam Monshipouri
(74) *Attorney, Agent, or Firm* — Schwegman Lundberg & Woessner, P.A.

(57) ABSTRACT

This invention relates to a novel formaldehyde dehydrogenase expressed by a formaldehyde dehydrogenase gene and having independent reduction activity for formic acid, a method of preparing the formaldehyde dehydrogenase from a strain transformed with a recombinant expression vector including the gene, and a method of producing formaldehyde from formic acid through a reduction reaction of the formaldehyde dehydrogenase.

1 Claim, 4 Drawing Sheets

US 9,963,684 B2

FORMALDEHYDE DEHYDROGENASE AND METHOD FOR PREPARING FORMALDEHYDE USING SAME

PRIORITY APPLICATIONS

This application is a U.S. National Stage under 35 U.S.C. 371 from International Application No. PCT/KR2014/004812, filed on 29 May 2014, and published as WO2015/137565 on 17 Sep. 2015, which claims the benefit of priority to Korean Application No. 10-2014-0029848, filed on 13 Mar. 2014; which applications and publication are incorporated herein by reference in their entirety.

TECHNICAL FIELD

The present invention relates to a novel formaldehyde dehydrogenase and a method of producing formaldehyde using the same and, more particularly, to a *Burkholderia multivorans* (KTCT 2970)-derived novel formaldehyde dehydrogenase and a method of producing formaldehyde from formic acid using the formaldehyde dehydrogenase in the presence of an NADH coenzyme.

BACKGROUND ART

The industrial use of biocatalytic reactions is rapidly growing with the advancement of biotechnology because various catalytic reactions, including reactions that have not conventionally been able to be carried out using conventional chemical catalysts, are performed under biocompatible conditions.

Such reactions are typically applied to the synthesis of chiral compounds, alcohols, aldehydes, amino acids and medical intermediates, the synthesis of polymers suitable for biodegradable or biometric applications, and the development of biosensors for assays and diagnosis. Furthermore, because of current problems attributable to an increase in the concentration of carbon dioxide and global warming resulting therefrom, thorough research into decreasing carbon dioxide emissions and producing a new type of energy through the reduction reaction of carbon dioxide is ongoing in academic and industrial fields. Specifically, carbon dioxide is converted into formic acid using a formate dehydrogenase, the produced formic acid is converted into formaldehyde by means of a formaldehyde dehydrogenase, and the formaldehyde is converted into methanol by means of an alcohol dehydrogenase. For this, the formaldehyde dehydrogenase must be essentially contained in a multi-enzyme system. Despite its potential importance and usability, there have been almost no reports on reduction reactions involving formaldehyde dehydrogenase, compared to oxidation reactions thereof. Since the oxidation reaction, rather than the reduction reaction, is carried out in a thermodynamically favorable and feasible manner due to the properties of typical dehydrogenase, formaldehyde dehydrogenase having independent reduction activity has not yet been reported.

Therefore, a novel formaldehyde dehydrogenase, having independent reducibility for converting formic acid into formaldehyde, needs to be reliably applicable to a multi-enzyme system so that methanol can be produced using carbon dioxide, and moreover, so that a variety of industrially important chemicals can be produced.

DISCLOSURE

Technical Problem

Accordingly, the present invention has been made keeping in mind the problems encountered in the art, and a first object of the present invention is to provide a formaldehyde dehydrogenase for independently reducing formic acid.

A second object of the present invention is to provide a formaldehyde dehydrogenase gene encoding the formaldehyde dehydrogenase.

A third object of the present invention is to provide a recombinant expression vector including the formaldehyde dehydrogenase gene.

A fourth object of the present invention is to provide all transformed strains, including transformed recombinant *E. coli*.

A fifth object of the present invention is to provide a method of preparing a recombinant formaldehyde dehydrogenase using the transformed strain.

The other objects and advantageous of the present invention will be understood more clearly based on the following description, claims and drawings.

Technical Solution

In order to accomplish the above objects, the present invention provides a formaldehyde dehydrogenase having reduction activity, comprising the amino acid sequence of SEQ ID NO:2.

In an embodiment of the present invention, the formaldehyde dehydrogenase is preferably derived from *Burkholderia multivorans* but may be prepared through genetic engineering methods or chemical synthesis methods.

In an embodiment of the present invention, the formaldehyde dehydrogenase of the present invention may have a molecular weight of 41.5 kDa.

In addition, the present invention provides a formaldehyde dehydrogenase gene encoding the formaldehyde dehydrogenase of the invention.

In an embodiment of the present invention, the gene preferably comprises a base sequence of SEQ ID NO:1, which has a homology of at least 85%, preferably at least 90%, and more preferably 95% with the sequence of SEQ ID NO:2, taking into consideration degeneracy of the genetic code, but the present invention is not limited thereto.

In addition, the present invention provides a recombinant expression vector including the formaldehyde dehydrogenase gene of the invention.

In addition, the present invention provides a method of producing a formaldehyde dehydrogenase by culturing a strain transformed using the recombinant expression vector of the invention.

In addition, the present invention provides a method of producing formaldehyde from a substrate through a reduction reaction of the formaldehyde dehydrogenase of the invention by treating the substrate with the formaldehyde dehydrogenase.

In an embodiment of the present invention, the substrate is preferably formic acid, but the present invention is not limited thereto.

In addition, the present invention provides a composition for producing formaldehyde, containing the formaldehyde dehydrogenase of the invention as an active ingredient.

Hereinafter, a description will be given of the present invention.

The present invention addresses a *Burkholderia multivorans* (KTCT 2970)-derived novel formaldehyde dehydrogenase, which is able to produce formaldehyde from formic acid, and also provides reaction conditions for efficiently producing formaldehyde from formic acid using the above enzyme system.

In the present invention, a formaldehyde dehydrogenase gene is cloned from *Burkholderia multivorans* through southern hybridization and colony hybridization. In the method of producing formaldehyde according to the present invention, a formate dehydrogenase derived from *Burkholderia multivorans* (KTCT 2970) is produced.

The present invention is specified below.

In the present invention, the formaldehyde dehydrogenase has the amino acid sequence represented by SEQ ID NO:2. Also, the formaldehyde dehydrogenase of the present invention encompasses a mutant formaldehyde dehydrogenase, resulting from at least one mutation of deletion, substitution and addition of at least one amino acid within a range within which the activity of the formaldehyde dehydrogenase represented by the protein having the corresponding amino acid sequence is not impaired, with respect to the amino acid sequence of SEQ ID NO:2.

In addition, the present invention addresses a formaldehyde dehydrogenase gene encoding the formaldehyde dehydrogenase having the amino acid sequence of SEQ ID NO:2, and the sequence of the gene is represented by SEQ ID NO: 1. Also, the formaldehyde dehydrogenase gene of the present invention encompasses a mutant formaldehyde dehydrogenase gene encoding the mutant formaldehyde dehydrogenase, obtained by mutating the base sequence of SEQ ID NO:1.

In addition, the present invention addresses a recombinant vector containing the formaldehyde dehydrogenase gene and a transforming transformed using the recombinant vector. Furthermore, the present invention addresses a method of preparing a formaldehyde dehydrogenase comprising separating a formaldehyde dehydrogenase from a culture product obtained by culturing the transforming.

The formaldehyde dehydrogenase gene of the present invention is separated from the cell mass of *Burkholderia multivorans* (KTCT 2970). Specifically, chromosomal DNA is acquired from a strain having a formaldehyde dehydrogenase gene, after which a polymerase chain reaction (PCR) is carried out using a designed oligonucleotide as a primer and chromosomal DNA of a *Burkholderia multivorans* (KTCT 2970) strain as a template, so that the formaldehyde dehydrogenase gene is partially amplified. Thereby, the PCR amplification fragment thus obtained is a fragment having approximately 100% homology with the formaldehyde dehydrogenase gene of the *Burkholderia tradhvorans* (KTCT 2970) strain, whereby it may be expected to have high S/N ratio as a probe when colony hybridization is performed and also makes it easy to control the stringency of hybridization. The PCR amplification fragment is labeled using an appropriate reagent, the chromosomal DNA library is subjected to colony hybridization, and the formaldehyde dehydrogenase gene is selected (Current Protocols in Molecular Biology, vol. 1, pp. 603, 1994).

The plasmid is recovered from *E. coli*, selected by the above method, using an alkali method (Current Protocols in Molecular Biology, vol. 1, pp. 161, 1994), thereby obtaining a DNA fragment containing the formaldehyde dehydrogenase gene. After the determination of the base sequence using the above method, the DNA fragment having the base sequence is decomposed using a restriction enzyme to formulate a DNA fragment that is then used as a probe, followed by hybridization, thereby yielding all genes of the present invention. SEQ ID NO:1 shows the base sequence of the formaldehyde dehydrogenase gene of the present invention and SEQ ID NO:2 shows the amino acid sequence encoded by the gene.

The transformed microorganism of the present invention is obtained by introducing the recombinant vector of the present invention into a host suitable for the expression vector that is used when manufacturing the recombinant vector. The expression vector used in the present embodiment is pET28a, but any expression vector may be used so long as it satisfies the above requirements.

The formaldehyde dehydrogenase of the present invention is prepared in a manner in which a transforming, obtained by transforming the host using the recombinant vector having the gene encoding the formaldehyde dehydrogenase, is cultured, a formaldehyde dehydrogenase, as a genetic product, is produced and accumulated in the culture product (cultured cell mass or supernatant), and then the enzyme is acquired from the culture product.

The acquisition and purification of the formaldehyde dehydrogenase may be performed by recovering the cell mass or supernatant from the culture product through centrifugation, followed by lysis of cell mass, affinity chromatography, and cationic or anionic exchange chromatography, which are used alone or in combination.

In order to develop a formaldehyde dehydrogenase that exhibits reducibility in the present invention, the formaldehyde dehydrogenase gene is cloned from *Burkholderia multivorans* (KTCT 2970). Thus, formaldehyde is able to be obtained from formic acid through a reduction reaction of the expressed recombinant *Burkholderia multivorans* (KTCT 2970)-derived formaldehyde dehydrogenase using NADH as a coenzyme, thus culminating in the present invention.

In order to prepare industrially useful formaldehyde dehydrogenase, the gene encoding the formaldehyde dehydrogenase is cloned from the gene of *Burkholderia multivorans* (KTCT 2970), and the base sequence of the above gene and the amino acid sequence derived therefrom are analyzed. The formaldehyde dehydrogenase of the present invention is an enzyme that catalyzes the reduction reaction using formic acid as a substrate to form formaldehyde, and is preferably a formaldehyde dehydrogenase that is specific for a reduction reaction and is capable of converting formic acid into formaldehyde.

The formaldehyde dehydrogenase of the present invention has the following features: (i) the molecular weight thereof is about 41.5 kDa; (ii) a conventional formaldehyde dehydrogenase alone seldom shows activity for reducing formic acid into formaldehyde, but the sole use of the formaldehyde dehydrogenase of the present invention enables the reduction of formic acid in the presence of an NADH coenzyme, without the use of a multi-enzyme system, thereby producing formaldehyde. Therefore, the enzyme of the present invention for producing formaldehyde from formic acid is very specific, and may be efficiently applied to the production of formaldehyde through a biocatalytic reaction in an economical manner.

Advantageous Effects

According to the present invention, the *Burkholderia multivorans*-derived formaldehyde dehydrogenase is able to reduce formic acid in the presence of an NADH coenzyme to thereby efficiently produce formaldehyde.

MODE FOR INVENTION

A better understanding of the present invention may be obtained via the following examples, which are set forth to illustrate, but are not to be construed as limiting the present invention.

EXAMPLE 1: Cloning of Novel Formaldehyde Dehydrogenase Gene from *Burkholderia multivorans*

In the case of genes having similar functions, individual base sequences and sizes are known to be similar to some extent. Thus, the gene of formaldehyde dehydrogenase of *Burkholderia multivorans* is estimated to have a size of about 1.2 kb, and all genes of formaldehyde dehydrogenase of *Burkholderia multivorans* were cloned based on already known formaldehyde dehydrogenase base sequences of other strains.

An *E. coli* pET28a vector was used in the cloning process. An LB medium having a typical composition was used for culturing *E. coli*, and culturing of *Burkholderia multivorans* was performed on malt extract peptone agar. The plate media of *E. coli*, were an LB agar plate and an agar plate composed of 3 to 5% of sugar, 0.3 to 0.5% of a beef extract, 0.9 to 1.1% of Bacto peptone, and 1.3 to 1.7% of agar. If necessary, 50 μg/ml of ampicillin was added. *Burkholderia multivorans* was inoculated into a 250 ml Erlenmeyer flask containing 50 ml of a culture medium and cultured at 37° C. and 200 rpm for 5 days, and *E. coli* was cultured at 37° C. and 200 rpm for 16 hr.

Most DNA was identified on agarose gel (TAE buffer, 0.5%) using an electrophoresis method, and the DNA band was purified on the gel using a QiaXII gel extraction device (QIAGEN, USA), and DNA ligation was used T4 DNA ligase (NEB). Also, RNA extraction of *Burkholderia multivorans* was performed using a Qiagen plant total RNA kit (QIAGEN), and the reverse transcriptase for the synthesis of cDNA was Oligo-dT RT-mix (Intron).

In order to clone the formaldehyde dehydrogenase gene, the *Burkholderia multivorans* chromosome was separated. To partially amplify the *Burkholderia multivorans* formaldehyde dehydrogenase gene, nonspecific primers (degenerated primers), BinFalDH_5'-SP1 atttgyggcagcgatcwrcatatg-kwysrc (SEQ ID NO:3) and BmFaIDH_3'-SP1-Attggcrthccgggnytgtaygtgmcc (SEQ ID NO:4) were manufactured, based on the already known formaldehyde dehydrogenase base sequences of other strains, and were used so that a portion of the formaldehyde dehydrogenase gene 780 bp long was amplified in the *Burkholderia multivorans* chromosome using PCR.

Figure 1:
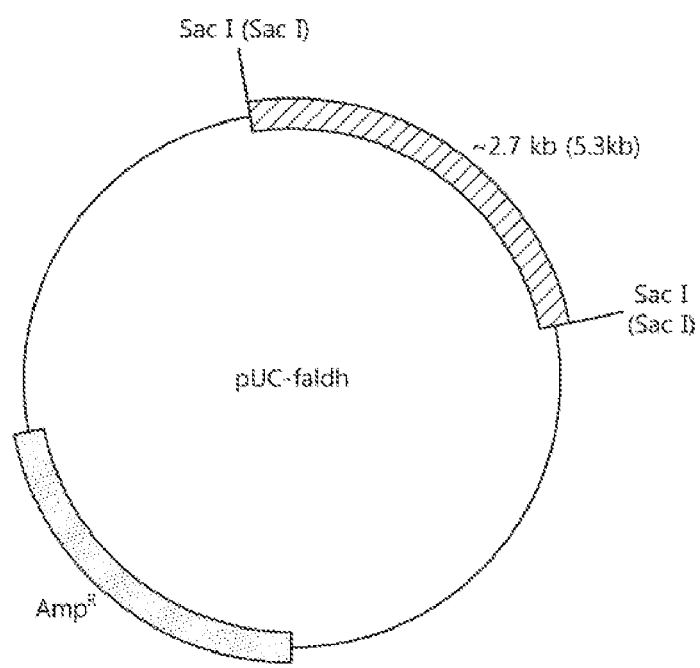
FIG. 1 shows the vector map of vector pET28a in which a fragment having a formaldehyde dehydrogenase gene, selected from chromosomes of *Burkholderia multivorans* (KTCT 2970), is cloned into a vector used for *E. coli*.

Using Sac1, Not1, Xho1 and Sal1 as restriction enzymes having no restriction sites in the base sequence of the amplified portion as above, genomic DNA of *Burkholderia multivorans* was completely cleaved. Furthermore, a radio-labeled probe was manufactured using the DNA fragment obtained by PCR, and was used to search for a DNA fragment having a gene of interest through southern hybridization. A desired gene was searched for using a fragment cut with Sac1 of about 2.7 kb and a fragment cut with Sal1 of about 5.3 kb. A DNA fragment of about 2.7 kb, separated after cleavage of the *Burkholderia multivorans* chromosome with Sac1, and a DNA fragment of about 5.3 kb, cut with Sal1, were cloned into WC and called pUC-faldh (FIG. 1).

Colony hybridization was performed using the probe having a size of 780 bp in the pUC-faldh library, and thus a clone having the desired formaldehyde dehydrogenase gene was determined. The base sequence was analyzed using the determined clone, whereby the total 1,197 bp-long gene base sequence of formaldehyde dehydrogenase was found (SEQ ID NO:1), and had a size similar to the formaldehyde dehydrogenase gene as proven in the other strains.

EXAMPLE 2: Preparation of Recombinant Expression Vector and Recombinant Strain

Figure 2:
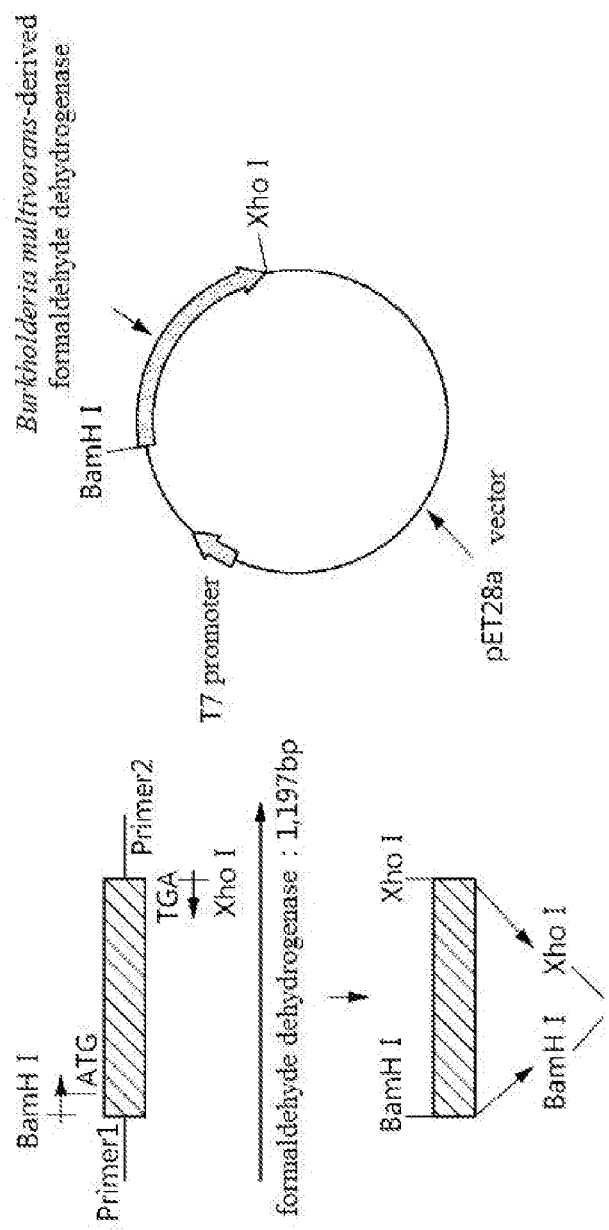
FIG. 2 shows a process of manufacturing an expression vector including the formaldehyde dehydrogenase gene derived from *Burkholderia multivorans*.

In order to express a large amount of formaldehyde dehydrogenase in *E. coli* using the gene encoding formaldehyde dehydrogenase of Example 1, the enzyme gene was inserted into BarriFIT and Xho1 sites of the expression vector pET28a (Novagen, USA) and then transformed to *E. coli* B1-21 (DE3) (NEB, England) (FIG. 2).

EXAMPLE 3: Expression of Recombinant Formaldehyde Dehydrogenase and Isolation

Figure 3:
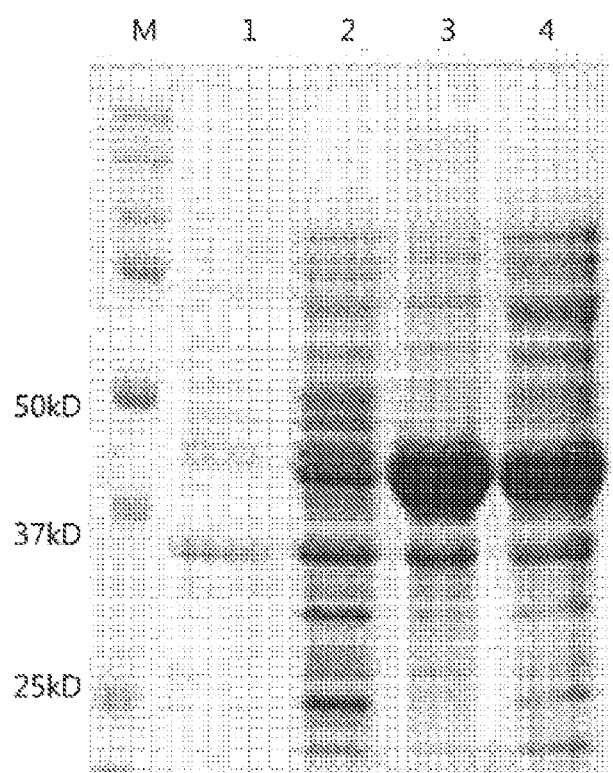
FIG. 3 shows the SDS-PAGE gel of formaldehyde dehydrogenase derived from *Burkholderia multivorans*, 1 indicating the size marker, 2 indicating the water-soluble protein expressed using a strain transformed with an expression vector, 3 indicating the insoluble protein of formaldehyde dehydrogenase, and 4 indicating the water-soluble protein of formaldehyde dehydrogenase.

The recombinant strain of Example 2 was inoculated into an LB medium and cultured at 37° C. for 24 hr, and the protein expressed on the SDS-PAGE gel was identified (FIG. 3).

In order to purify the recombinant formaldehyde dehydrogenase expressed using the method of Example 2, the recombinant strain culture solution was centrifuged (8000× g, 10 min), and only the cell mass was collected and sonicated to thus lyse the cell wall of *E. coli*, followed by centrifugation at 20,000×g for 20 min to remove the precipitate (cell mass), thus yielding the supernatant. Thereafter, final Ni-NTA His-tag interaction chromatography (Qiagen, Germany) was performed, thereby isolating a recombinant formaldehyde dehydrogenase.

EXAMPLE 4: Optimal pH for Producing Formaldehyde Through Reduction Reaction

The test for the production of formaldehyde using the formaldehyde dehydrogenase of Example 3 was performed under the following conditions. In the method of producing formaldehyde of the present invention using the formaldehyde dehydrogenase, the amount of formaldehyde that was produced was measured depending on changes in pH during the reaction.

Figure 4:
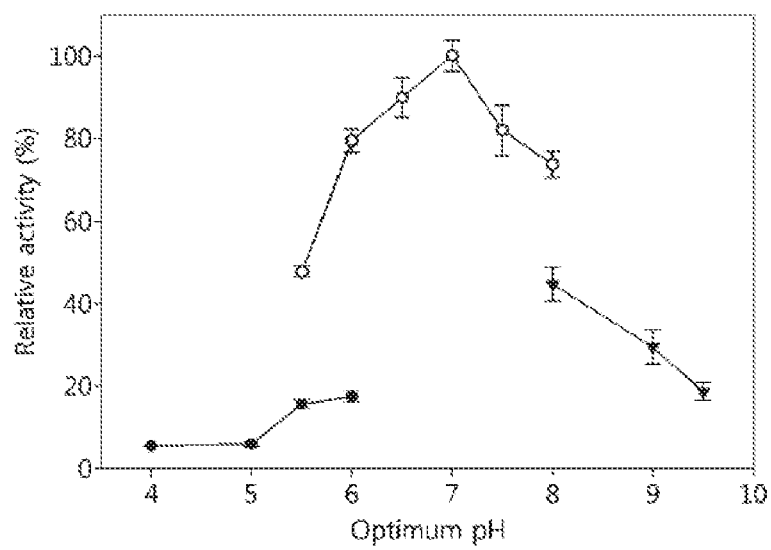
FIG. 4 shows the optimal pH for producing formaldehyde through a reduction reaction.

Enzyme purification was carried out as in Example 3, and the amount of formaldehyde that was produced was measured using a 100 mM substrate solution at 25° C. in the pH range of 4.0 to 10.0. As shown in FIG. 4, the amount of formaldehyde that was produced was the greatest at pH 7.0. Thus, the optimal pH was determined to be 7.0 in the method of producing formaldehyde of the present invention.

EXAMPLE 5: Metal Ion Effect

In order to evaluate the effect of the metal ion of the purified formaldehyde dehydrogenase on enzymatic activity, this test was performed. Each of $MgCl_2$, $MnCl_2$, $CoCl_2$, $ZnCl_2$, $FeCl_2$, $CuSO_4$, $CoCl_2$, $HgCl_2$, $BaCl$ and $KCl$ at final concentrations of 1 mM and 5 mM was added to the enzyme reaction solution, and residual activity of the enzyme was measured. The effects of various metals at concentrations of 1 mM and 5 mM on formaldehyde dehydrogenase activity are shown in Table 1 below. The formaldehyde dehydrogenase of the present invention exhibited 2.7 times as much enzyme activity in the presence of 5 frill $Mg^{2+}$ than without it (Table 1).

TABLE 1

| Metal ions | Relative activity (%) 1 mM | Relative activity (%) 5 mM |
|---|---|---|
| $MnCl_2$ | 62.32 | 111.6 |
| $MgCl_2$ | 147.8 | 269.6 |
| $CaCl_2$ | 50.67 | 75.96 |
| $ZnCl_2$ | 63.99 | 192.2 |
| $CuSO_4$ | 124.3 | 91.30 |
| $CoCl_2$ | 58.39 | 72.60 |
| $BaCl_2$ | 98.55 | 115.1 |
| KCl | 104.0 | 94.49 |
| $FeCl_2$ | ND | ND |
| $HgCl_2$ | ND | ND |
| None | 15.00 | 13.00 |

Table 1 shows the effects of metal ions on the activity of formaldehyde dehydrogenase.

EXAMPLE 6: Kinetic Parameters of Formaldehyde Dehydrogenase

Figure 5:
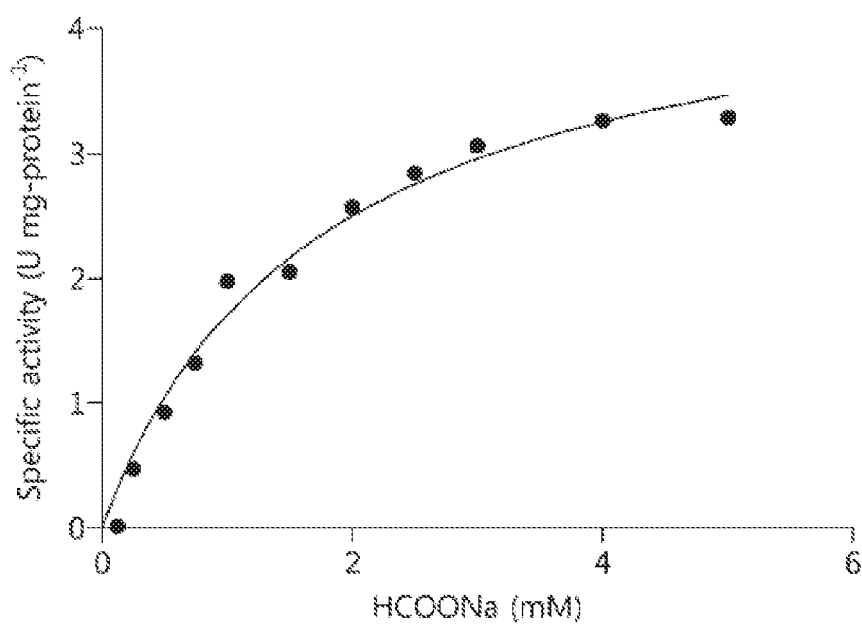
FIG. 5 is a graph showing the kinetic parameters of formaldehyde dehydrogenase.

Enzymatic reaction was carried out using formic acid as a substrate at various concentrations (0.125 to 5 mM), after which kinetic parameters thereof were measured through nonlinear regression analysis (FIG. 5). As for the formaldehyde dehydrogenase, the $K_m$ value for NADH was determined to be about 0.19 mM, and the $K_m$ value for—formic acid was about 1.7 mM, Vmax being determined to be about 4.7 U mg-protein$^{-1}$.

EXAMPLE 7: Test for Producing Formaldehyde from Formic Acid

The test for producing formaldehyde using *Burkholderia multivorans*-derived formaldehyde dehydrogenase was carried out under optimal conditions. A 10 mM substrate was reacted with 20 μg of formaldehyde dehydrogenase in the reaction solution for 3 hr under conditions of a pH of 7.0 and a reaction temperature of 30° C., whereby a conversion rate of about 27% resulted. This is the first report on the direct production of formaldehyde from formic acid through hioconversion.

The invention claimed is:

1. A method of producing formaldehyde from a substrate through a reduction reaction with formaldehyde dehydrogenase having reduction activity and comprising an amino acid sequence of SEQ ID NO:2 by treating the substrate with the formaldehyde dehydrogenase using NADH as a coenzyme, wherein the substrate is formic acid.

* * * * *

SEQUENCE LISTING

```
<160> NUMBER OF SEQ ID NOS: 4

<210> SEQ ID NO 1
<211> LENGTH: 1197
<212> TYPE: DNA
<213> ORGANISM: Burkholderia multivorans

<400> SEQUENCE: 1
atgagcagca atcgtggcgt tgtttacctg ggtccgggca aagtggaagt tcagaaaatc      60
gactatccga aaatggttga tccgagcggt cgtgcaattg ccacggtgt tatcctgaaa      120 gtggttagca ccaacatttg tggttctgat cagcatatgg tccgtggtcg taccacggca      180
ccggtcggtc tggtgctggg ccacgaaatt accggtgaag tcgtggaagt cggccgcgat      240
gtggaaacgc tgaaaatcgg tgacctggtt tcagtcccgt ttaatgttgc ctgcggtcgt      300
tgtgcaatgt gcaaagaaac ccatacgggc gtttgtctga acgtcaatcc gtcgcgcgcc      360
ggcggtgcat atggttacgt ggatatgggc ggttggatcg gcggtcaggc cgaatatgtg      420
ctggttccgt acgcagactt taacctgctg aaattcccgg atcgtgacca agcaatggct      480
aaaattcgcg atctgacctg cctgagcgac atcctgccga cgggctatca tggtgctgtg      540
agtgcgggtg ttaaaccggg ctccaccgtc tacattgcag gtgcaggtcc ggtgggtatg      600
gcagcagcag ctagcgcacg tctgctgggt gcagcagtta cgatcgtcgg cgatatgaac      660
gcagaacgcc tggcacacgc taaagcgatg ggctttgaaa ccgtggatct gtctaaagac      720
gctacgctgg gtgaacagat tgcgcaaatc ctgggcaaac cggaaattga ttgtgctgtg      780
gactgcgttg gtttcgaagc gcatggccac ggtagctctg gccatgccga agaagccccg      840
gcaaccgttc tgaattcact gatggaaatt acgcgtccgg ctggtgcaat tggtatcccg      900
ggtctgtatg tgaccgatga cccgggtgcg caggataaag cagctcaaca tggcagtctg      960
tccatccgct tcggcctggg ttgggccaaa tcacactcgt ttttcaccgg ccagacgccg     1020
gttctgaaat ataaccgtaa tctgatgcaa gccattctgt acgatcgcct gccgattgca     1080
```

```
aaaatcgtca atgtgaccgt tatctccctg gatgacgctc cggaaggtta caaaaaattt    1140
gatggcggtg cgccgcgtaa attcgtgatt gacccgcacg gcctgctggc agcctaa      1197
```

<210> SEQ ID NO 2
<211> LENGTH: 398
<212> TYPE: PRT
<213> ORGANISM: Burkholderia multivorans

<400> SEQUENCE: 2

Met Ser Ser Asn Arg Gly Val Val Tyr Leu Gly Pro Gly Lys Val Glu
1 5 10 15

Val Gln Lys Ile Asp Tyr Pro Lys Met Val Asp Pro Ser Gly Arg Ala
20 25 30

Ile Gly His Gly Val Ile Leu Lys Val Val Ser Thr Asn Ile Cys Gly
35 40 45

Ser Asp Gln His Met Val Arg Gly Arg Thr Thr Ala Pro Val Gly Leu
50 55 60

Val Leu Gly His Glu Ile Thr Gly Glu Val Val Glu Val Gly Arg Asp
65 70 75 80

Val Glu Thr Leu Lys Ile Gly Asp Leu Val Ser Val Pro Phe Asn Val
85 90 95

Ala Cys Gly Arg Cys Ala Met Cys Lys Glu Thr His Thr Gly Val Cys
100 105 110

Leu Asn Val Asn Pro Ser Arg Ala Gly Gly Ala Tyr Gly Tyr Val Asp
115 120 125

Met Gly Gly Trp Ile Gly Gly Gln Ala Glu Tyr Val Leu Val Pro Tyr
130 135 140

Ala Asp Phe Asn Leu Leu Lys Phe Pro Asp Arg Asp Gln Ala Met Ala
145 150 155 160

Lys Ile Arg Asp Leu Thr Cys Leu Ser Asp Ile Leu Pro Thr Gly Tyr
165 170 175

His Gly Ala Val Ser Ala Gly Val Lys Pro Gly Ser Thr Val Tyr Ile
180 185 190

Ala Gly Ala Gly Pro Val Gly Met Ala Ala Ala Ala Ser Ala Arg Leu
195 200 205

Leu Gly Ala Ala Val Thr Ile Val Gly Asp Met Asn Ala Glu Arg Leu
210 215 220

Ala His Ala Lys Ala Met Gly Phe Glu Thr Val Asp Leu Ser Lys Asp
225 230 235 240

Ala Thr Leu Gly Glu Gln Ile Ala Gln Ile Leu Gly Lys Pro Glu Ile
245 250 255

Asp Cys Ala Val Asp Cys Val Gly Phe Glu Ala His Gly His Gly Ser
260 265 270

Ser Gly His Ala Glu Glu Ala Pro Ala Thr Val Leu Asn Ser Leu Met
275 280 285

Glu Ile Thr Arg Pro Ala Gly Ala Ile Gly Ile Pro Gly Leu Tyr Val
290 295 300

Thr Asp Asp Pro Gly Ala Gln Asp Lys Ala Ala Gln His Gly Ser Leu
305 310 315 320

Ser Ile Arg Phe Gly Leu Gly Trp Ala Lys Ser His Ser Phe Phe Thr
325 330 335

Gly Gln Thr Pro Val Leu Lys Tyr Asn Arg Asn Leu Met Gln Ala Ile
340 345 350

Leu Tyr Asp Arg Leu Pro Ile Ala Lys Ile Val Asn Val Thr Val Ile

```
               355                 360                 365
Ser Leu Asp Asp Ala Pro Glu Gly Tyr Lys Lys Phe Asp Gly Gly Ala
    370                 375                 380

Pro Arg Lys Phe Val Ile Asp Pro His Gly Leu Leu Ala Ala
385                 390                 395

<210> SEQ ID NO 3
<211> LENGTH: 30
<212> TYPE: DNA
<213> ORGANISM: Artificial Sequence
<220> FEATURE:
<223> OTHER INFORMATION: A synthetic primer

<400> SEQUENCE: 3
atttgyggca gcgatcwrca tatgkwysrc                                30

<210> SEQ ID NO 4
<211> LENGTH: 27
<212> TYPE: DNA
<213> ORGANISM: Artificial Sequence
<220> FEATURE:
<223> OTHER INFORMATION: A synthetic primer
<221> NAME/KEY: misc_feature
<222> LOCATION: (1)...(27)
<223> OTHER INFORMATION: n = A,T,C or G

<400> SEQUENCE: 4
attggcrthc cgggnytgta ygtgmcc                                   27
```